United States Patent [19]

Agbodoe et al.

[11] Patent Number: 5,284,129
[45] Date of Patent: Feb. 8, 1994

[54] SWIVEL RING SURGICAL RETRACTOR

[75] Inventors: Victor B. Agbodoe, Boston; Edward L. Gallini, Marion; Robert E. David, Duxbury, all of Mass.

[73] Assignee: Codman & Shurtleff, Inc., Randolph, Mass.

[21] Appl. No.: 936,970

[22] Filed: Aug. 28, 1992

[51] Int. Cl.$^5$ ............................................. A61B 17/02
[52] U.S. Cl. ........................................ 128/20; 128/17; 606/130; 403/84
[58] Field of Search ............................ 128/20, 17-19; 403/83, 150, 17, 18, 84, 321, 322; 606/1, 130, 54, 56, 59; 248/316.5, 316.6, 291

[56] References Cited

U.S. PATENT DOCUMENTS

| | | | |
|---|---|---|---|
| 1,839,726 | 1/1932 | Arnold . | |
| 2,594,086 | 4/1952 | Smith | 128/20 |
| 3,129,706 | 4/1964 | Reynolds, Jr. | 128/20 |
| 3,522,799 | 8/1970 | Gauthier | 128/20 |
| 4,099,521 | 7/1978 | Nestor, et al. | 128/20 |
| 4,254,763 | 3/1981 | McCready, et al. | 128/20 |
| 4,434,791 | 3/1984 | Darnell | 128/20 |
| 4,457,300 | 7/1984 | Budde | 128/20 |
| 5,009,124 | 4/1991 | Beaurepaire et al. | 403/150 X |
| 5,201,742 | 4/1993 | Hasson | 606/130 |
| 5,214,815 | 6/1993 | Agbodoe et al. | 5/637 |

OTHER PUBLICATIONS

Codman Surgical Products Catalog, 1990, p. N-120.

*Primary Examiner*—Richard J. Apley
*Assistant Examiner*—Donna L. Maraglio
*Attorney, Agent, or Firm*—Michael Q. Tatlow

[57] ABSTRACT

A swivel ring surgical retractor in a generally circular form is disclosed. The retractor has a fixed portion which is attached to the operating table or other support and a portion which can swivel in relationship to the fixed portion. The swivel portion is attached to the fixed portion of the retractor with a threaded shaft which forces two sunburst clamping inserts into engagement to secure the swivel portion to the fixed portion. The swivel portion can be adjusted or removed from the fixed portion by unthreading the shaft to disengage the sunburst clamping inserts to adjust the position of the swivel portion or to remove the swivel portion from the fixed portion.

3 Claims, 3 Drawing Sheets

SWIVEL RING SURGICAL RETRACTOR

FIELD OF THE INVENTION

The invention relates to the field of surgical appliances and particularly to a device that is used to mount surgical retractors in a position over the body of the patient and more particularly over the head of the patient during a surgical procedure.

BACKGROUND OF THE INVENTION

Surgical retractors are used for holding tissue, at the edge of a surgical incision or wound, away from the field of the operation. One particular type of retractor employs a support mechanism to which the actual retractor elements can be attached. This type of retractor is commonly used in abdominal surgery and also in brain surgery. In abdominal surgery the retractor is positioned over the abdomen of the patient. Moveable retractor arms are positioned to hold body tissue surrounding the incision away from the field of the operation. In brain surgery, the retractor is similarly used to keep tissue away from the field of the surgical procedure.

A particular type of retractor used in both abdominal and brain surgery is a retractor which has a frame to which individual arms, having retractor blades at their ends, can be attached. The positioning of the retractor on the frame can be adjusted so that the retractor can be used to adjust the retractor blades in the proper position for different types of surgery.

Examples of such retractors are those disclosed in U.S. Pat. Nos. 1,839,726; 2,594,086; 3,522,799; 4,099,521; 4,254,763 and 4,457,300. All of these retractors include a frame to which different types of retractor elements can be attached. The retractor blades themselves can be adjusted to position the retractor blades in a proper location to keep tissue away from the operative field during the surgical procedure. The retractor disclosed in U.S. Pat. No. 4,099,521 is a ring shape retractor in which a portion of the ring is removable.

The retractor disclosed in U.S. Pat. No. 4,457,300 is ring shaped and has a dovetail slot around the outer circumference of the ring. The disclosure of U.S. Pat. No. 4,457,300 is incorporated herein by reference. Retractor elements can be fitted into the dovetail slot and secured in various positions. An improvement to the ring shown in U.S. Pat. No. 4,457,300 provides a two component ring which has a portion which can swivel 180° to provide greater access to the operative site if desired. The swivel portion of the ring is attached to the fixed portion with a pair of pivot mechanisms which fit into the dovetail slot around the outer circumference of the ring. There is a sunburst clamp on one side of the ring which may be disengaged to allow the swivel portion of the ring to rotate. The swivel portion of the ring also can be removed from the fixed portion of the ring by the removal of the pivot mechanisms from the dovetail slot on opposite sides of the fixed portion of the ring.

SUMMARY OF THE INVENTION

The present invention provides an improved swivel ring retractor mechanism which provides the ability to swivel a portion of the ring in an 180° arc as well as to readily remove the swivel portion of the ring from the fixed portion of the ring if the removal of a portion of the ring is desired to provide greater access to the surgical field.

In the surgical retractor of the present invention, the swivel portion of the retractor ring can be removed by one person without the necessity of employing any tools. The swivel portion of the ring is attached to the fixed portion of the ring with a removable pin which is centered in a sunburst clamp and has a bore into which a pin located on the fixed portion of the ring can be inserted.

DETAIL DESCRIPTION OF THE INVENTION

Figure 1:
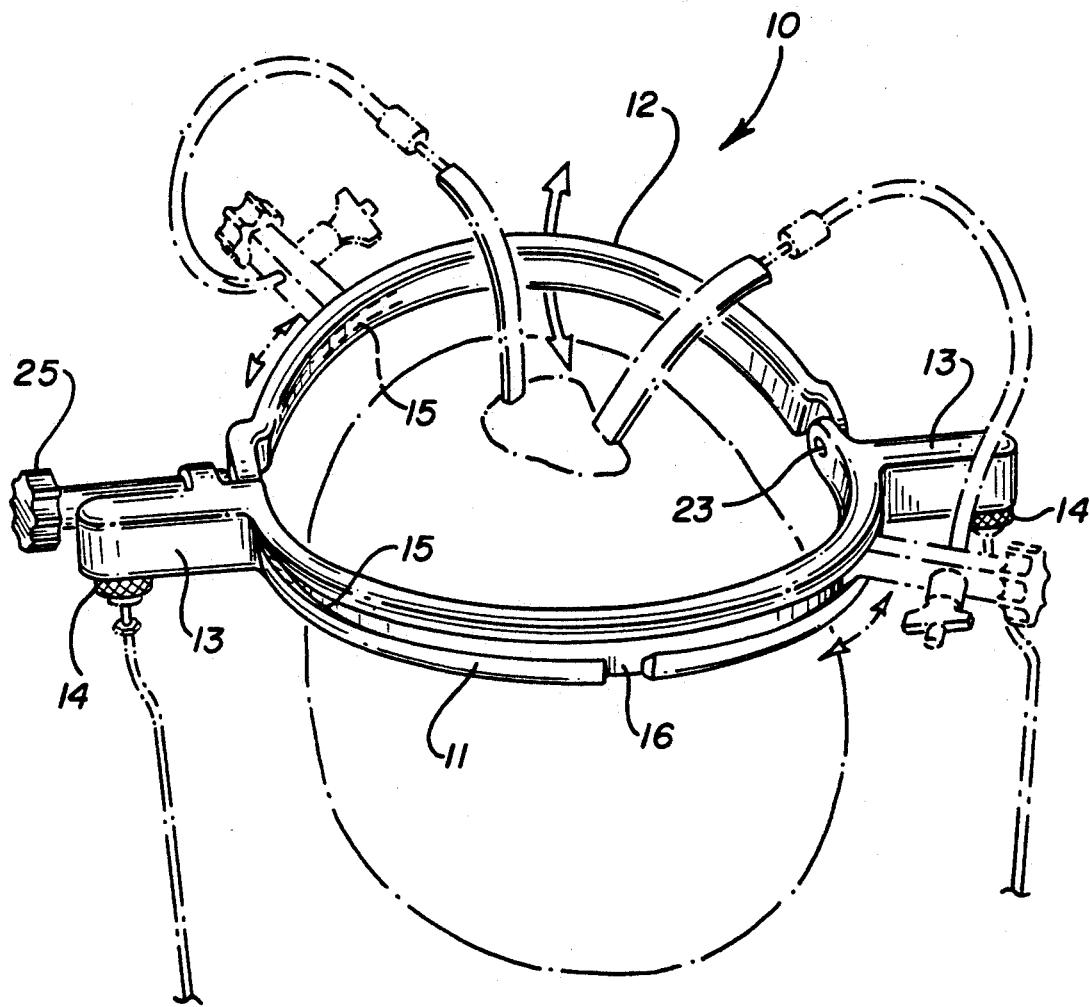
FIG. 1 is a perspective view of the retractor ring of the present invention.
Figure 2:
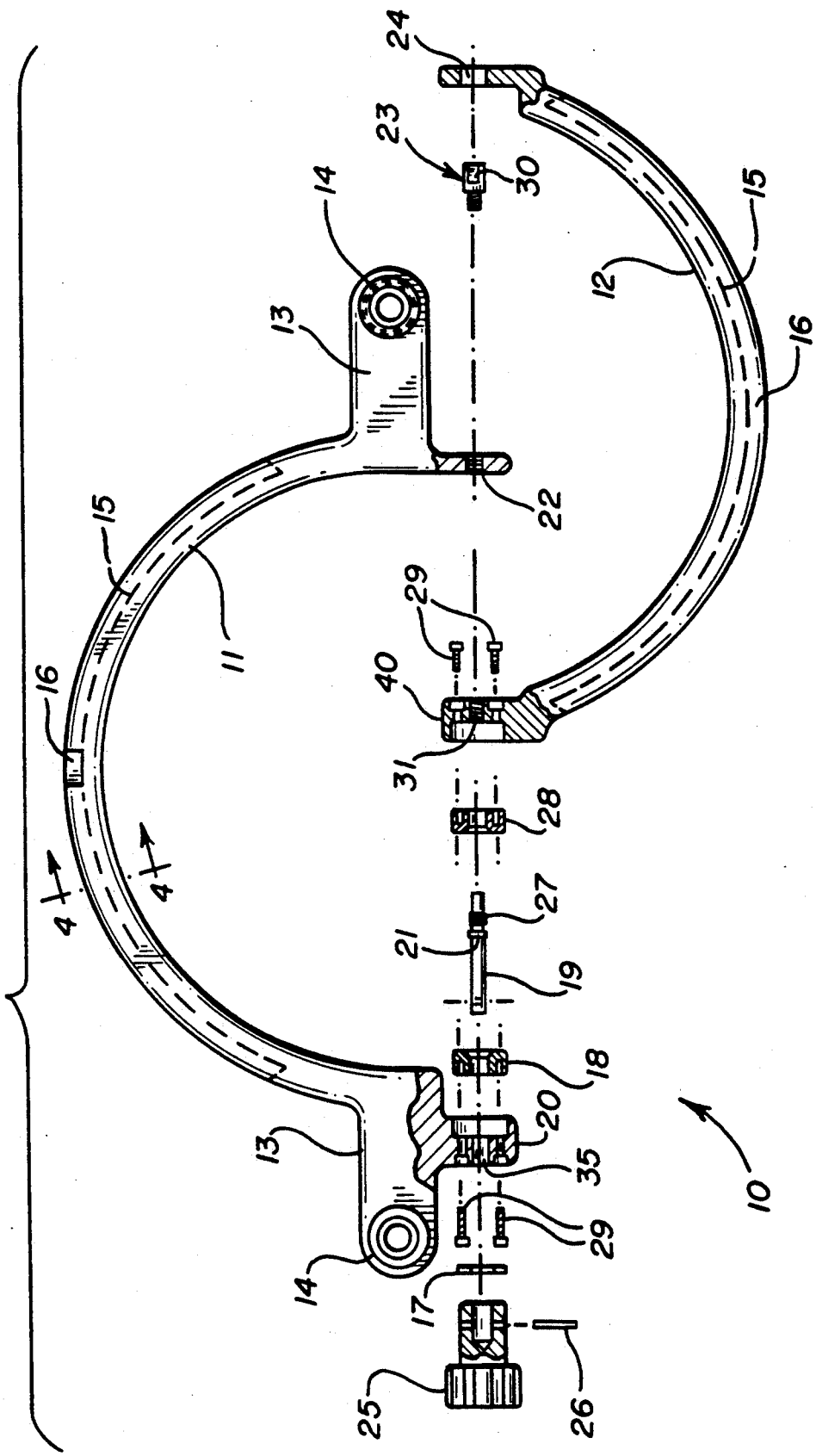
FIG. 2 is a bottom plan view partially in section of a disassembled ring of the present invention.
Figure 3:
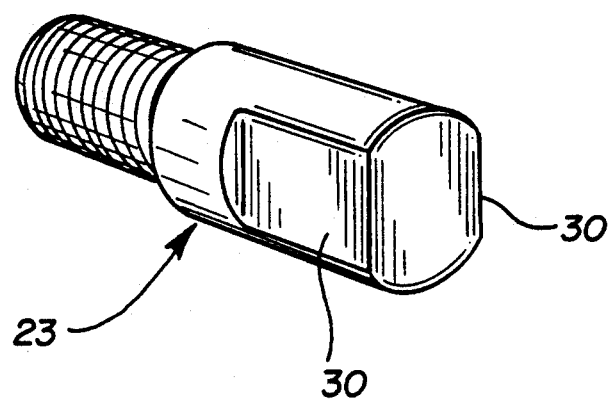
FIG. 3 is a perspective view of the shoulder pin used to support the swivel portion of the ring of the present invention.
Figure 4:
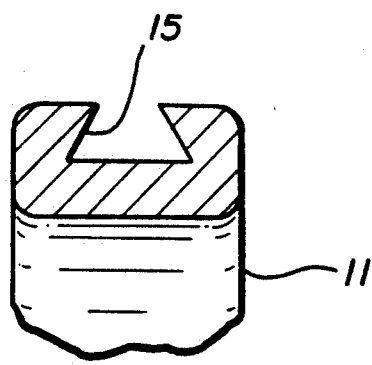
FIG. 4 is a cross sectional view of the ring structure showing the dovetail groove as taken along line 4—4 of FIG. 2.

As shown in FIG. 1, the retractor ring of the present invention comprises a generally circular ring 10 which is made in two parts, a fixed portion 11 and a swivel portion 12. The fixed portion 11 has two support arms 13 that extend outwardly from the circumference of the ring. On the lower portion of each of the support arms there is a threaded bushing 14 which is adapted to receive a ball which can be fixed to a support rod (shown in phantom) to secure the retractor ring to an operating room table or other support. A support mechanism of this type is shown in detail in U.S. Pat. No. 4,457,300 mentioned above. Around the outer circumference of the ring there is a dovetail slot 15 which extends substantially around the circumference of each portion of the ring. There is an opening 16, preferably in the lower surface of each portion of the ring, to allow fixtures which secure the retractor blades to be inserted into the dovetail slot. Adjacent the support arm on one side of the retractor ring there is a first boss 20 which has a sunburst clamping insert 18 affixed thereto. Through the center of the sunburst insert and boss 20 there is a bore 35 into which shaft 19 extends. There is a handle 25 secured to the outwardly directed portion of the shaft by pin 26. The handle 25 extends outwardly beyond the adjacent support arm 13 to provide ready access and ease in manipulation of the handle. There is a washer 17 between the handle 25 and the first boss to allow ease of rotation of the handle. There is a threaded end 27 on the inwardly directed portion of the shaft. There is a step 21 immediately outward of the threaded end 27 of the shaft to hold the shaft into the sunburst clamping insert 18. The portion of the shaft located on the inward extremity has no threads but is used as a pivot to position the shaft into an opening in a sunburst clamping insert 28 of a second boss 40 on the swivel portion 12 of the retractor. The sunburst clamping inserts 18 and 28 are held into the respective portion of the rings by screw 29. There is a second opening or threaded bore 22 on the opposite side of the fixed ring directly in line with the shaft 19. A pin 23 is threaded into the bore 22.

The ring has a swivel portion 12 which is capable of swiveling 180° along an axis between the threaded shaft 19 and the outwardly directed pin 23 on the fixed portion 11 of the ring and which is aligned with the shaft 19. The pin 23 has at least one and preferably two flat shoulders 30 so that the pin can freely rotate in the bore or opening 24 of the swivel ring without binding. In the swivel portion of the ring there is a sunburst clamping insert 28 which is mated with the sunburst clamping insert 18 on the fixed portion of the ring to securely prevent the swivel portion of the ring from rotating until desired. Second boss 40 of the swivel portion of the ring has an internally threaded bore 31 in its center. The threads in the bore are matched with the threads on the shaft 19. There is a second bore 24 on the swivel portion of the ring which is aligned with the threaded bore 31 to receive the pin 23 on the fixed portion of the ring.

In use, the ring is mounted on the supports by inserting a ball into the bushings 14 in the support arms 13. A locking ring is used to secure the support to the support arm. Retractors of the type shown in U.S. Pat. No. 4,457,300 can be fitted into the dovetail slot and positioned around the surgical incision. The retractor blades are held in the slot 15 by dovetail clamps which can be moved to position the retractors in the position desired by the surgeon.

In use, if it is desired to rotate the swivel portion of the ring into a different position, the handle 25 on the shaft 19 can be rotated to remove the threaded end of the shaft from the threads in the swivel portion of the swivel ring. This allows the sunbursts clamping inserts to disengage and the swivel portion of the ring can rotate around an axis made up of the shaft 19 and the pin 23.

In the event it is desired to totally remove the swivel portion of the ring, the handle 25 can be rotated to totally remove the threaded end 27 of the shaft from the sunburst insert 28 in the swivel portion of the ring. The pin 23 will then disengage from the bore 24 and the swivel portion of the retractor ring can be totally removed from the fixed portion of the ring.

We claim:

1. In a generally circular hinged surgical retractor for retaining tissue in a retracted position in a surgical incision including a generally semi-circular fixed portion and a generally semi-circular swivel portion secured together to allow movement of said swivel portion relative to said fixed portion and an outwardly directed channel around the major portion of the circumference of each of said fixed and swivel portions to receive a retractor arm holder to which a retractor blade may be attached and support means on said fixed portion to hold the retractor in a position over an incision, the improvement comprising a first boss having an inwardly directed sunburst clamping insert located on said fixed portion, a second boss having an outwardly directed sunburst clamping insert located on the swivel portion, a threaded opening centrally located in said second boss insert, a rotatable handle affixed to a shaft extending through said first boss and said inwardly directed sunburst clamping insert to engage said outwardly directed sunburst clamping insert, and said threaded opening in said second boss and a screw thread on an inward portion of said shaft, and said shaft having an inward extremity having no threads, an outwardly directed swivel pin on the fixed portion which is aligned with the shaft, a smooth walled bore on the swivel portion to receive the swivel pin, the swivel portion being releasably secured to the fixed portion by said screw thread, said first and second bosses and said sunburst clamping inserts to allow movement of said swivel portion relative to said fixed portion and the separation of said swivel portion from said fixed portion.

2. The improved surgical retractor of claim 1 in which the support means on said fixed portion comprise at least two arms which extend outwardly from the circumference of said fixed portion, wherein one of said arms is adjacent said rotatable handle, and wherein said rotatable handle extends outwardly beyond said one of said arms adjacent thereto to provide access to said handle.

3. The improved surgical retractor of claim 1 in which the outwardly directed swivel pin is cylindrical and has a flattened shoulder to prevent binding in said bore upon rotation of the swivel portion of the retractor.

* * * * *